(12) United States Patent
Dormitzer et al.

(10) Patent No.: US 8,883,481 B2
(45) Date of Patent: Nov. 11, 2014

(54) REVERSE GENETICS METHODS FOR VIRUS RESCUE

(75) Inventors: Philip Dormitzer, Weston, MA (US); Björn Keiner, Marburg (DE); Pirada Suphaphiphat, Brookline, MA (US); Michael Franti, Quebec (CA); Peter Mason, Sommerville, MA (US); Jennifer Uhlendorff, Neuss (DE); Mikhail Matrosovich, Marburg (DE)

(73) Assignee: Novartis AG, Basel (CH)

( * ) Notice: Subject to any disclaimer, the term of this patent is extended or adjusted under 35 U.S.C. 154(b) by 17 days.

(21) Appl. No.: 13/503,353

(22) PCT Filed: Oct. 20, 2010

(86) PCT No.: PCT/IB2010/054752
§ 371 (c)(1),
(2), (4) Date: Oct. 11, 2012

(87) PCT Pub. No.: WO2011/048560
PCT Pub. Date: Apr. 28, 2011

(65) Prior Publication Data
US 2013/0034582 A1    Feb. 7, 2013

Related U.S. Application Data

(60) Provisional application No. 61/279,487, filed on Oct. 20, 2009.

(51) Int. Cl.
*C12N 7/00* (2006.01)
*C12N 7/02* (2006.01)
*A61K 39/145* (2006.01)

(52) U.S. Cl.
CPC ........ *C12N 7/00* (2013.01); *C12N 2760/16151* (2013.01)
USPC ...................... 435/239; 435/235.1; 424/206.1

(58) Field of Classification Search
CPC ........... C12N 7/00; C12N 2760/16151; C12N 2760/16251; C12N 2760/16152; C12N 2760/16252; C12N 2760/16134; C12N 2760/16234; A61K 39/145
See application file for complete search history.

(56) References Cited

U.S. PATENT DOCUMENTS 6,455,298 B1 * 9/2002 Groner et al. .............. 435/235.1
2008/0124803 A1  5/2008 Billeter et al.

FOREIGN PATENT DOCUMENTS

| WO | WO-2003/091401 | 4/2003 |
| WO | WO-2005/062820 | 7/2005 |
| WO | WO-2007/047459 | 7/2005 |
| WO | WO-2010/046335 | 4/2010 |

OTHER PUBLICATIONS

Wang et al. Cloning of the canine RNA polymerase I promoter and establishment of reverse genetics for influenza A and B in MDCK cells. Virology Journal 2007, vol. 4, p. 102-113.*
Nicolson et al. Generation of influenza vaccine viruses on Vero cells by reverse genetics: an H5N1 candidate vaccine strain produced under a quality system. Vaccine 2005, vol. 23, pp. 2943-2952.*
Koudstaal et al. (Apr. 28, 2009). "Suitability of Per.C6 cells to generate epidemic and pandemic influenza vaccine strains by reverse genetics." Vaccine 27(19):2588-93.
Neumann (2003). "Reverse genetics for the control of avian influenza," Avian Dis. 47(3 Suppl):882-7.
Suphaphiphat et al. (Apr. 2010). "Human RNA Polymerase I-Driven Reverse Genetics for Influenza A Virus in Canine Cells," J. Virol. vol. 84 No. 7 3721-3725.
Whiteley et al. (Jul. 2007). "Generation of candidate human influenza vaccine strains in cell culture—rehearsing the European response to an H7N1 pandemic threat," Influenza Other Respi Viruses. 1(4):157-66.
Zhang et al. (Sep. 2009). "A one-plasmid system to generate influenza virus in cultured chicken cells for potential use in influenza vaccine," J Virol. 83(18):9296-303.
International Search Report mailed on Feb. 21, 2012, for International Patent Application No. PCT/IB2010/054752, filed on Oct. 20, 2010.
International Preliminary Report on Patentability mailed on Jul. 27, 2012, for International Patent Application No. PCT/IB2010/054752, filed on Oct. 20, 2010.
Xuan, Bai (2008). "The Construction of Rotavirus Group a Reassortment strain by Reverse Genetics," China Master's Thesis Full Text Database, No. 12. Available online at <http://www.dissertationtopic.net/doc/1470105>.

* cited by examiner

*Primary Examiner* — Louise Humphrey
(74) *Attorney, Agent, or Firm* — Atsuko Polzin; Otis Littlefield

(57) ABSTRACT

A method for rescuing a virus by reverse genetics is provided in which cells are added after transfection.

8 Claims, 4 Drawing Sheets

SEQUENCE LISTING

```
<160> NUMBER OF SEQ ID NOS: 4

<210> SEQ ID NO 1
<211> LENGTH: 566
<212> TYPE: PRT
<213> ORGANISM: Influenza A virus

<400> SEQUENCE: 1

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30
```

```
Val Asp Thr Val Leu Glu Lys Asn Val Thr Val Thr His Ser Val Asn
         35                  40                  45
Leu Leu Glu Asp Lys His Asn Gly Lys Leu Cys Lys Leu Arg Gly Val
 50                  55                  60
Ala Pro Leu His Leu Gly Lys Cys Asn Ile Ala Gly Trp Ile Leu Gly
 65                  70                  75                  80
Asn Pro Glu Cys Glu Ser Leu Ser Thr Ala Ser Ser Trp Ser Tyr Ile
                 85                  90                  95
Val Glu Thr Pro Ser Ser Asp Asn Gly Thr Cys Tyr Pro Gly Asp Phe
             100                 105                 110
Ile Asp Tyr Glu Glu Leu Arg Glu Gln Leu Ser Ser Val Ser Ser Phe
         115                 120                 125
Glu Arg Phe Glu Ile Phe Pro Lys Thr Ser Ser Trp Pro Asn His Asp
 130                 135                 140
Ser Asn Lys Gly Val Thr Ala Ala Cys Pro His Ala Gly Ala Lys Ser
145                 150                 155                 160
Phe Tyr Lys Asn Leu Ile Trp Leu Val Lys Lys Gly Asn Ser Tyr Pro
                 165                 170                 175
Lys Leu Ser Lys Ser Tyr Ile Asn Asp Lys Gly Lys Glu Val Leu Val
             180                 185                 190
Leu Trp Gly Ile His His Pro Ser Thr Ser Ala Asp Gln Gln Ser Leu
         195                 200                 205
Tyr Gln Asn Ala Asp Thr Tyr Val Phe Val Gly Ser Ser Arg Tyr Ser
 210                 215                 220
Lys Lys Phe Lys Pro Glu Ile Ala Ile Arg Pro Lys Val Arg Asp Gln
225                 230                 235                 240
Glu Gly Arg Met Asn Tyr Tyr Trp Thr Leu Val Glu Pro Gly Asp Lys
                 245                 250                 255
Ile Thr Phe Glu Ala Thr Gly Asn Leu Val Val Pro Arg Tyr Ala Phe
             260                 265                 270
Ala Met Glu Arg Asn Ala Gly Ser Gly Ile Ile Ile Ser Asp Thr Pro
         275                 280                 285
Val His Asp Cys Asn Thr Thr Cys Gln Thr Pro Lys Gly Ala Ile Asn
 290                 295                 300
Thr Ser Leu Pro Phe Gln Asn Ile His Pro Ile Thr Ile Gly Lys Cys
305                 310                 315                 320
Pro Lys Tyr Val Lys Ser Thr Lys Leu Arg Leu Ala Thr Gly Leu Arg
                 325                 330                 335
Asn Ile Pro Ser Ile Gln Ser Arg Gly Leu Phe Gly Ala Ile Ala Gly
             340                 345                 350
Phe Ile Glu Gly Gly Trp Thr Gly Met Val Asp Gly Trp Tyr Gly Tyr
         355                 360                 365
His His Gln Asn Glu Gln Gly Ser Gly Tyr Ala Ala Asp Leu Lys Ser
 370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                 405                 410                 415
Leu Glu Lys Arg Ile Glu Asn Leu Asn Lys Lys Val Asp Asp Gly Phe
             420                 425                 430
Leu Asp Ile Trp Thr Tyr Asn Ala Glu Leu Leu Val Leu Leu Glu Asn
         435                 440                 445
Glu Arg Thr Leu Asp Tyr His Asp Ser Asn Val Lys Asn Leu Tyr Glu
```

```
                450             455             460
Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                    485                 490                 495

Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 2
<211> LENGTH: 566
<212> TYPE: PRT
<213> ORGANISM: Influenza A virus

<400> SEQUENCE: 2

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Asn His Asn Gly Lys Leu Cys Lys Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Ser Trp Ser Tyr Ile
                85                  90                  95

Ala Glu Thr Pro Asn Ser Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Lys His Asn
        130                 135                 140

Val Thr Lys Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Ser Ser His Tyr Asn
    210                 215                 220

Arg Arg Phe Thr Pro Glu Ile Ala Lys Arg Pro Lys Val Arg Asn Gln
225                 230                 235                 240

Glu Gly Arg Ile Asn Tyr Tyr Trp Thr Leu Leu Glu Pro Gly Asp Thr
                245                 250                 255
```

```
Ile Ile Phe Glu Ala Asn Gly Asn Leu Ile Ala Pro Trp Tyr Ala Phe
                260                 265                 270

Ala Leu Ser Arg Gly Phe Gly Ser Gly Ile Ile Thr Ser Asn Ala Ser
            275                 280                 285

Met Asp Glu Cys Asp Ala Lys Cys Gln Thr Pro Gln Gly Ala Ile Asn
        290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Ile Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 3
<211> LENGTH: 469
<212> TYPE: PRT
<213> ORGANISM: Influenza A virus

<400> SEQUENCE: 3

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60
```

```
Thr Tyr Val Asn Ile Ser Asn Thr Asn Phe Ala Ala Gly Gln Ser Val
 65                  70                  75                  80

Val Ser Val Lys Leu Ala Gly Asn Ser Ser Leu Cys Pro Val Ser Gly
             85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
            115                 120                 125

Cys Arg Thr Phe Phe Leu Thr Gln Gly Ala Leu Leu Asn Asp Lys His
            130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
                180                 185                 190

Ile Gly Ile Ser Gly Pro Asp Asn Gly Ala Val Ala Val Leu Lys Tyr
            195                 200                 205

Asn Gly Ile Ile Thr Asp Thr Ile Lys Ser Trp Arg Asn Asn Ile Leu
210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
                260                 265                 270

Asn Tyr His Tyr Glu Glu Cys Ser Cys Tyr Pro Asp Ser Ser Glu Ile
            275                 280                 285

Thr Cys Val Cys Arg Asp Asn Trp His Gly Ser Asn Arg Pro Trp Val
            290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
            355                 360                 365

Asn Gly Phe Glu Met Ile Trp Asp Pro Asn Gly Trp Thr Gly Thr Asp
370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
            435                 440                 445

Asn Ser Asp Thr Val Gly Trp Ser Trp Pro Asp Gly Ala Glu Leu Pro
            450                 455                 460

Phe Thr Ile Asp Lys
465
```

<210> SEQ ID NO 4
<211> LENGTH: 470
<212> TYPE: PRT
<213> ORGANISM: Influenza A virus

<400> SEQUENCE: 4

```
Met Asn Pro Asn Gln Lys Ile Ile Thr Ile Gly Ser Ile Cys Met Thr
1               5                   10                  15

Ile Gly Ile Ile Ser Leu Ile Leu Gln Ile Gly Asn Ile Ile Ser Ile
            20                  25                  30

Trp Val Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
    50                  55                  60

Thr Tyr Val Asn Ile Asn Asn Thr Asn Val Val Ala Gly Lys Asp Thr
65                  70                  75                  80

Thr Ser Val Thr Leu Ala Gly Asn Ser Ser Leu Cys Pro Ile Arg Gly
                85                  90                  95

Trp Ala Ile Tyr Ser Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Ala Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asp Gly Ala Val Ala Val Leu Lys Tyr
        195                 200                 205

Asn Gly Ile Ile Thr Glu Thr Ile Lys Ser Trp Arg Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Pro Ala Ser Tyr Arg Ile Phe
                245                 250                 255

Lys Ile Glu Lys Gly Lys Ile Thr Lys Ser Ile Glu Leu Asp Ala Pro
            260                 265                 270

Asn Ser His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Lys Gly Ser Cys Asp
                325                 330                 335

Pro Val Thr Val Asp Gly Ala Asp Gly Val Lys Gly Phe Ser Tyr Arg
            340                 345                 350

Tyr Gly Asn Gly Val Trp Ile Gly Arg Thr Lys Ser Asn Ser Ser Arg
        355                 360                 365

Lys Gly Phe Glu Met Ile Trp Asp Pro Asn Gly Trp Thr Asp Thr Asp
370                 375                 380
```

```
Ser Asn Phe Leu Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Val Arg Gly Arg Pro Arg
            420                 425                 430

Glu Gly Thr Thr Val Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp Lys
465             470
```

REVERSE GENETICS METHODS FOR VIRUS RESCUE

CROSS REFERENCE TO RELATED APPLICATIONS

This application is a U.S. National Phase patent application of PCT/IB2010/054752, filed Oct. 20, 2010, which claims priority to U.S. provisional patent application Ser. No. 61/279,487 filed Oct. 20, 2009, all of which are hereby incorporated by reference in the present disclosure in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 223002124600SeqList.txt, date recorded: Apr. 13, 2012, size: 18 KB).

TECHNICAL FIELD

This invention is in the field of reverse genetics. Furthermore, it relates to manufacturing vaccines for protecting against various viruses.

BACKGROUND ART

Reverse genetics permits the recombinant expression and manipulation of RNA viruses in cell culture. It is a powerful tool in virology and vaccine manufacture because it allows rapid production of recombinant viruses (including reassortants) and/or their mutation. The method involves transfecting host cells with one or more expression constructs that encode the viral genome and isolating the virus from the cells.

One drawback with virus rescue by reverse genetics is that the process is inefficient and frequently results in an unsatisfactory virus yield. Thus there remains a need in the art to provide alternative and more efficient reverse genetics methods.

SUMMARY OF PREFERRED EMBODIMENTS

The inventors have now surprisingly discovered that the poor efficiency of reverse genetics methods can be improved significantly by transfecting cells with the reverse genetics construct(s) and subsequently adding more cells to the transfected cells. The inventors surmise that the observed increase in efficiency is due to the fact that transfection is harmful to the cells. Thus, any viruses which are rescued need to expand in sick cells or wait until the virus is transferred to healthy cells. This results in a loss of viable virus. The addition of cells to the transfected host cells allows the rescued virus to multiply on a healthy cell substrate which increases the virus yield significantly.

In one embodiment, the invention provides a method for preparing a virus comprising the steps of (i) transfecting a culture of host cells with at least one expression construct encoding a viral RNA molecule; (ii) adding cells to the transfected host cells of (i) to provide a mixture of cells; and (iii) culturing the mixture of cells in order to produce virus.

In a further embodiment, the invention provides a method of preparing a virus for vaccine manufacture, comprising the steps of (i) transfecting a culture of host cells with at least one expression construct encoding a viral RNA molecule; (ii) adding cells to the transfected host cells of (i) to provide a mixture of cells; (iii) culturing the mixture of cells in order to produce virus; (iv) purifying the virus obtained in step (iii) and optionally (v) formulating the virus into a vaccine.

Reverse Genetics

Reverse genetics can be used for the production of a wide variety of RNA viruses, including positive-strand RNA viruses [1,2], negative-strand RNA viruses [3,4] and double-stranded RNA viruses [5]. Thus, the present invention provides a method for producing a recombinant virus wherein the virus is obtained using the reverse genetics method of the present invention.

Known reverse genetics systems involve expressing DNA molecules which encode desired viral. RNA (vRNA) molecules from pol I promoters, bacterial RNA polymerase promoters, bacteriophage polymerase promoters, etc. Furthermore, where a virus requires certain proteins to form an infectious virus, the systems also provide these proteins e.g. the system further comprises DNA molecules that encode viral proteins such that expression of both types of DNA leads to assembly of a complete infectious virus.

Where reverse genetics is used for the expression of vRNA, it will be evident to the person skilled in the art that precise spacing of the sequence elements with reference to each other is pivotal for the polymerase to initiate replication. It is therefore important that the DNA molecule encoding the viral RNA is positioned correctly between the pol I promoter and the termination sequence, but this positioning is well within the capabilities of those who work with reverse genetics systems.

Generally, reverse genetics is suitable for expression of any viruses which are known to require production of genomic RNA during their life-cycle. Such viruses include, but are not limited to, positive-strand and negative-strand RNA viruses, such as those described below. Preferably, the virus is an orthomyxovirus, e.g., an influenza virus. The methods of the invention are further suitable for non-segmented as well as segmented viruses.

Where the virus is a positive-strand RNA virus it is often sufficient to transfect a cell with an expression construct comprising the viral genome. For example, the transfection of plasmids containing the poliovirus genome resulted in the recovery of infectious poliovirus [1,2]. Reverse genetics for negative-strand RNA viruses has presented more challenges as the antisense viral RNA is usually non-infective and requires an RNA polymerase to complete the life cycle. Thus, the viral polymerase must be supplied, either as protein or as a gene for in situ protein expression.

Where the virus requires a protein for infectivity, it is generally preferred to use bi-directional expression constructs as this reduces the total number of expression constructs required by the host cell. Thus, the method of the invention may utilise at least one bi-directional expression construct wherein a gene or cDNA is located between an upstream pol II promoter and a downstream non-endogenous pol I promoter. Transcription of the gene or cDNA from the pol II promoter produces capped positive-sense viral mRNA which can be translated into a protein, while transcription from the non-endogenous pol I promoter produces negative-sense vRNA. The bi-directional expression construct may be a bi-directional expression vector.

In order to produce a recombinant virus, a cell must express all segments of the viral genome which are necessary to assemble a virion. DNA cloned into the expression constructs of the present invention preferably provides all of the viral RNA and proteins, but it is also possible to use a helper virus to provide some of the RNA and proteins, although systems which do not use a helper virus are preferred. Where the virus is a non-segmented virus this can usually be achieved by utilising a single expression construct in the method of the invention, even though it is also within the scope of the invention to express the viral genome of non-segmented viruses using more than one expression construct. Where the virus is a segmented virus, the viral genome is usually expressed using more than one expression construct in the method of the invention. It is also envisioned, however, to combine one or more segments or even all segments of the viral genome on a single expression construct.

Methods of the invention are particularly suitable for the production of reassortant virus strains. The technique can use in vitro manipulation of plasmids to generate combinations of viral segments, to facilitate manipulation of coding or noncoding sequences in the viral segments, to introduce mutations, etc. The use of the expression system for the production of reassortant virus strains is preferred as this can significantly decrease the time needed to obtain a reassortant seed virus which is particularly beneficial in situations where a rapid production of vaccine is needed to counteract an epidemic. Thus, it is preferred that the method of this aspect of the invention uses one or more expression constructs that express viral genes from or derived from at least two different wild type strains.

An expression construct which leads to expression of an accessory protein in the host cell can also be used. For instance, it can be advantageous to express a non-viral serine protease (e.g. trypsin) as part of a reverse genetics system.

Expression Constructs

The expression constructs encoding the viral RNA molecules for use in the invention can be any expression construct commonly used in the art to rescue viruses.

The expression constructs used may be uni-directional or bi-directional expression constructs. Where a host cell expresses more than one transgene (whether on the same or different expression constructs) it is possible to use uni-directional and/or bi-directional expression.

Bi-directional expression constructs contain at least two promoters which drive expression in different directions (i.e. both 5' to 3' and 3' to 5') from the same construct. The two promoters can be operably linked to different strands of the same double stranded DNA. Preferably, one of the promoters is a pol I promoter and at least one of the other promoters is a pol II promoter. This is useful as the pol I promoter can be used to express uncapped cRNAs while the pol II promoter can be used to transcribe mRNAs which can subsequently be translated into proteins, thus allowing simultaneous expression of RNA and protein from the same construct.

The expression construct (whether uni-directional or bi-directional) will typically include an RNA transcription termination sequence. The termination sequence may be an endogenous termination sequence or a termination sequence which is not endogenous to the host cell. Suitable termination sequences will be evident to those of skill in the art and include, but are not limited to, RNA polymerase I transcription termination sequence, RNA polymerase II transcription tea initiation sequence, and ribozymes. Furthermore, the expression constructs may contain one or more polyadenylation signals for mRNAs, particularly at the end of a gene whose expression is controlled by a pol II promoter.

The pol I and pol II promoters used in the expression constructs can be derived from an organism in the same taxonomic order as the host cell in which the expression construct is expressed. Alternatively, the promoters can be derived from an organism in a different taxonomic order than the host cell. The term "order" refers to conventional taxonomic ranking, and examples of orders are primates, rodentia, carnivora, marsupialia, cetacean, etc. Humans and chimpanzees are in the same taxonomic order (primates), but humans and dogs are in different orders (primates vs. carnivora).

In the methods of the invention, a host cell may be transfected with at least two, at least three, at least four, at least five, at least six, at least seven, at least eight, at least nine, at least ten, at least eleven or at least twelve expression constructs.

An expression construct may be a vector, such as a plasmid or other episomal construct. Such vectors will typically comprise at least one bacterial and/or eukaryotic origin of replication. Furthermore, the vector may comprise a selectable marker which allows for selection in prokaryotic and/or eukaryotic cells. Examples of such selectable markers are genes conferring resistance to antibiotics, such as ampicillin or kanamycin. The vector may further comprise one or more multiple cloning sites to facilitate cloning of a DNA sequence.

As an alternative, an expression construct may be a linear expression construct. Such linear expression constructs will typically not contain any amplification and/or selection sequences. However, linear constructs comprising such amplification and/or selection sequences are also within the scope of the present invention. An example of a method using such linear expression constructs for the expression of influenza virus is described in reference 6.

Expression constructs of the invention can be generated using methods known in the art. Such methods were described, for example, in reference 7. Where the expression construct is a linear expression construct, it is possible to linearise it before introduction into the host cell utilising a single restriction enzyme site. Alternatively, it is possible to excise the expression construct from a vector using at least two restriction enzyme sites. Furthermore, it is also possible to obtain a linear expression construct by amplifying it using a nucleic acid amplification technique (e.g. by PCR).

Where the expression host is a canine cell, such as a MDCK cell line, protein-coding regions may be optimised for canine expression e.g. using a promoter from a wild-type canine gene or from a canine virus, and/or having codon usage more suitable for canine cells than for human cells. For instance, whereas human genes slightly favour UUC as the codon for Phe (54%), in canine cells the preference is stronger (59%). Similarly, whereas there is no majority preference for Ile codons in human cells, 53% of canine codons use AUC for Ile. Canine viruses, such as canine parvovirus (a ssDNA virus) can also provide guidance for codon optimisation e.g. 95% of Phe codons in canine parvovirus sequences are UUU (vs. 41% in the canine genome), 68% of Ile codons are AUU (vs. 32%), 46% of Val codons are GUU (vs. 14%), 72% of Pro codons are CCA (vs. 25%), 87% of Tyr codons are UAU (vs. 40%), 87% of His codons are CAU (vs. 39%), 92% of Gln codons are CAA (vs. 25%), 81% of Glu codons are GAA (vs. 40%), 94% of Cys codons are UGU (vs. 42%), only 1% of Ser codons are UCU (vs. 24%), CCC is never used for Phe and UAG is never used as a stop codon. Thus protein-coding genes can be made more like genes which nature has already optimised for expression in canine cells, thereby facilitating expression.

Transfection

"Transfection" refers to the introduction of DNA into a cell. The expression constructs can be introduced into host cells using any technique known to those of skill in the art. For example, they can be introduced into host cells by employing electroporation, DEAE-dextran, calcium phosphate precipitation, liposomes, microinjection, or microparticle-bombardment. Reverse genetics is commonly practised using the liposome method, for example using the transfection reagent Lipofectamine™. The methods of the invention are not restricted to transfection with liposomes, however, but are expected to work equally well with other transfection methods.

The cells can be added to the transfected host cells any time up to 72 hours after transfection. For example, the cells may be added immediately after transfection, 5 minutes, 10 minutes, 20 minutes, 30 minutes, 1 hour, 2 hours, 3 hours, 6 hours, 12 hours, 24 hours, 36 hours, 48 hours, 60 hours or 72 hours after transfection. Generally, the maximum time by which cells are added after transfection will match the maximum time for which the transfected cells can survive.

The period "after transfection" starts once the DNA has been introduced into host cells within the culture. The time point at which the DNA is introduced will vary with various factors, for example the cell line used, the method of transfection or the temperature at which transfection is performed. The time can be easily determined by the skilled person using standard methods. For example, several experiments can be conducted in parallel wherein the cells are transfected with reverse genetics constructs under identical conditions except that transfection is stopped at different time points. If the DNA has been introduced into the host cell then at least one virus should have formed. Thus, the skilled person can assay for the presence of a virus, for example by determining the number of plaque forming units using standard assays. The first time point after which at least one plaque forming unit (PFU) is detectable is the time point when the DNA has been introduced into the host cell.

Alternatively, the period after which cells are added to the transfected cells can be determined from the start of the transfection. The start of transfection is the time point at which the expression construct(s) encoding the viral molecule(s) are contacted with the culture of host cells. Thus, the cells can be added to the transfected cells any time up to 96 hours after the start of transfection, for example, 12 hours, 24 hours, 36 hours, 48 hours, 60 hours, 72 hours, 84 hours or 96 hours. While the time point "after transfection" and the time point "from the start of transfection" are measured relative to different starting points, the absolute time when the cells are added to the infected cells can be the same. For example, if it takes 1 hour for the DNA to be introduced into the host cells in a culture and the cells are added 30 minutes after the DNA has been introduced, then the cells would have been added 90 minutes from the start of transfection or 30 minutes after transfection.

The number of cells which are added after transfection will generally vary depending on the number of cells which are used as host cells for transfection and also on the size of the cell culture vessel which is used for transfection. The number of cells which could be used in the methods of the invention can be easily determined by the skilled person. For example, the methods of the invention can be performed under identical conditions in several parallel experiments except that the number of cells which are added differs. The number of cells which gives the highest virus yield can be used in further experiments. For example, when about $6 \times 10^5$ cells are used as a starting culture for transfection with Lipofectamine™, about $4 \times 10^5$ cells can be added.

The cells which are added after transfection provide a substrate for the rescued virus to replicate on. Thus, the cells may be uninfected cells which means that the cells, within a certain time (for example 48 hours) before they are used in the methods of the invention, have not been infected with a virus or transfected with an expression construct encoding a viral RNA. Cells which have been infected with a virus, for example Epstein-Barr virus, to immortalize them are suitable for use in the present invention. Likewise, transfected cells can be used in the methods of the present invention provided that transfection does not occur shortly (i.e. within 48 hours) before the cells are used in the methods of the present invention.

Where the rescued virus requires the presence of a protease for infectivity it will be advantageous to add the protease together with the cells after transfection. For example, the influenza virus requires the activity of a serine protease, like trypsin, for infection. Thus, when the method of the invention is used to rescue influenza viruses, the serine protease can be added at the same time as the cells after transfection. Alternatively, the protease can be added before or after the cells are added to the transfected cells.

Cells

The present invention can be practised with any eukaryotic cell that can produce the virus of interest. The invention will typically use a cell line although, for example, primary cells may be used as an alternative. The cell will typically be mammalian. Suitable mammalian cells include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [8-10]. Suitable dog cells are e.g. kidney cells, as in the CLDK and MDCK cell lines.

Further suitable cells include, but are not limited to: CHO; 293T; BHK; MRC 5; PER.C6 [11]; FRhL2; WI-38; etc. Suitable cells are widely available e.g. from the American Type Cell Culture (ATCC) collection [12], from the Coriell. Cell Repositories [13], or from the European Collection of Cell Cultures (ECACC). For example, the ATCC supplies various different Vero cells under catalogue numbers CCL 81, CCL 81.2, CRL 1586 and CRL-1587, and it supplies MDCK cells under catalogue number CCL 34. PER.C6 is available from the ECACC under deposit number 96022940. MDCK, Vero and PER.C6 cells are commonly used for the production of viruses and therefore each of these cells lines is particularly suitable for use with the methods of the present invention.

Preferred cells (particularly for growing influenza viruses) for use in the invention are MDCK cells [14-16], derived from Madin Darby canine kidney. The original MDCK cells are available from the ATCC as CCL 34. It is preferred that derivatives of these cells or derivatives of other MDCK cells are used. Derivatives of MDCK cells were described, for instance, in reference 14 which discloses MDCK cells that were adapted for growth in suspension culture ('MDCK 33016' or '33016-PF', deposited as DSM ACC 2219; see also ref. 14). Furthermore, reference 17 discloses MDCK-derived cells that grow in suspension in serum free culture ('B-702', deposited as FERM BP-7449). The MDCK cell line used may be tumorigenic. It is also envisioned to use non-tumorigenic MDCK cells. For example, reference 18 discloses non tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (ATCC PTA-6503). Reference 19 discloses MDCK cells with high susceptibility to infection, including 'MDCK.5F1' cells (ATCC CRL 12042).

The cells which are used for transfection and the cells which are added after transfection may be of the same or of a different cell type. For example, the expression constructs may be transfected into MDCK cells and the cells added may be Vero cells or vice versa. Another example may be methods where the expression constructs are transfected into one strain of MDCK cells and the cells added are of a different MDCK strain. This approach is advantageous where the rescued virus grows best in a cell line which can not easily be transfected. In this aspect, the virus can be transfected into cells which are more easily transfectable but can subsequently be propagated in a cell line which is better suited for viral replication. However, it is generally preferred to use the same cell line (e.g. MDCK 33016 cells) as a host cell for both transfection and for subsequent addition of cells as this has the advantage, for example, that competing culture selection pressures or different cell culture conditions can be avoided. It is also possible to use a mixture of more than one cell type as host cells for transfection and/or for addition after transfection.

Preferably, the cells are cultured in the absence of serum, to avoid a common source of contaminants. Various serum-free media for eukaryotic cell culture are known to the person skilled in the art (e.g. Iscove's medium, ultra CHO medium (BioWhittaker), EX-CELL (JRH Biosciences)). Furthermore, protein-free media may be used (e.g. PF-CHO (JRH Biosciences)). Otherwise, the cells for replication can also be cultured in the customary serum-containing media (e.g. MEM or DMEM medium with 0.5% to 10% of fetal calf serum).

The host cells and the cells which are added may be in adherent culture or in suspension culture. For example, the cells which are used for transfection can be adherent cells and the cells which are added after transfection can also be adherent cells. When the cells which are added after transfection are adherent cells, it will be evident that the cells will need to removed from the culture vessel on which they grow before they are added to the transfected cells. This can be achieved, for example, with the help of a serine protease like trypsin. It is also possible to use suspension cells as host cells for transfection and adherent cells for addition after transfection and vice versa.

The methods of the invention are usually practised at the temperatures which are commonly used in the art for the specific transfection method which is used. For example, when liposomes are used for transfection, the transfection reaction may initially be incubated at room temperature when the DNA/liposome complex is first added (e.g. for about 30 minutes), followed by incubation at about 37° C. for a specified period of time (for example about 24 hours). The methods of the invention can be practised with any transfection method known in the art and the temperatures at which transfection should be performed are therefore known to the skilled person. Alternatively, it is also possible to find suitable incubation temperatures by performing several transfection experiments in parallel under identical conditions except that the incubation temperature during transfection varies. The number of rescued viruses is indicative of the efficiency of transfection and can be determined by assaying for the number of PFUs produced, as described above. The temperature which results in the biggest number of PFUs can be used for transfection.

The temperature at which the cells are added to the transfected cells and the temperature at which the resulting mixture of cells is incubated may be the same or different compared to the temperature used during transfection. The temperature can depend on the cell line used for addition after transfection and can also vary with the virus which is rescued using the methods of the invention. Suitable temperatures for growing individual cell lines or rescuing particular viruses are known in the art, however, and the skilled person can therefore easily identify suitable temperatures. For example, mammalian cell lines like Vero, Per.C6 and MDCK cell lines are usually grown at a temperature between 36° C. and 38° C., or about 37° C. This temperature is also chosen for the rescue of many viruses, even though some viruses, like influenza, may be rescued at a temperature of about 33° C. as this can result in better antigenicity of the resulting virus [20]. Suitable temperatures can also be identified by performing several transfection experiments in parallel under identical conditions except that the incubation temperature after transfection varies. The temperature which results in the biggest number of PFUs can be used after transfection. Suitable methods for assaying for PFUs have been described above in relation to assays for identifying temperatures which can be used during transfection.

Virus Preparation

In a further aspect, the present invention provides a method of preparing a virus for vaccine manufacture, comprising the steps of (i) transfecting a culture of host cells with at least one expression construct encoding a viral RNA molecule; (ii) adding cells to the transfected host cells of (i) to provide a mixture of cells; (iii) culturing the mixture of cells in order to produce virus; and (iv) purifying the virus obtained in step (iii) and optionally (v) formulating the virus into a vaccine.

Where cells are used as a culture host in this aspect of the invention, it is known that cell culture conditions (e.g. temperature, cell density, pH value, etc.) are variable over a wide range subject to the cell line and the virus employed and can be adapted to the requirements of the application. The following information therefore merely represents guidelines.

As mentioned above, cells are preferably cultured in serum-free or protein-free media.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-hatch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients. It can be advantageous to adjust the value of the medium during multiplication of cells before infection to a value between pH 6.6 and pH 7.8 and especially between a value between pH 7.2 and pH 7.3. Culturing of cells preferably occurs at a temperature between 30 and 40° C. In step (iii), the cells are preferably cultured at a temperature of between 30° C. and 36° C. or between 32° C. and 34° C. or at about 33° C. This is particularly preferred where the method of the invention is used to produce influenza virus, as it has been shown that incubation of infected cells in this temperature range results in production of a virus that results in improved efficacy when formulated into a vaccine [20].

The oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about $8\text{-}25\times10^5$ cells/mL, in the batch system or preferably about $5\text{-}20\times10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

Virus may be grown on cells in adherent culture or in suspension. Microcarrier cultures can be used. Microcarrier cultures are considered adherent cultures. The cells may also be adapted for growth in suspension.

The methods according to the invention also include harvesting and isolation of viruses or the proteins generated by them. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

The viruses isolated according to the invention, can also be grown on eggs in step (iii). The current standard method for influenza virus growth for vaccines uses embryonated SPF hen eggs, with virus being purified from the egg contents (allantoic fluid). It is also possible to passage a virus through eggs and subsequently propagate it in cell culture.

Viruses

The methods of the invention may be practised with any virus which can be expressed by reverse genetics in a cell. Such viruses can be segmented or non-segmented viruses. Furthermore, the virus can be a positive-strand RNA virus or a negative-strand RNA virus. The virus may also be a double-stranded RNA virus.

Where the virus is a negative-strand RNA virus, the virus may be from a family selected from the group consisting of Paramyxoviridae, Pneumovirinae, Rhabdoviridae, Filoviridae, Bornaviridae, Orthomyxoviridae, Bunyaviridae, or Arenaviridae. Furthermore, the virus may be a virus from a genus selected from the group consisting of Paramyxovirus, Orthomyxovirus, Respirovirus, Morbillivirus, Rubulavirus, Henipaviras, Avulavirus, Pneumovirus, Metapneumovirus, Vesiculovirus, Lyssavirus, Ephemerovirus, Cytorhabdovirus, Nucleorhabdovirus, Novirhabdovirus, Marburgvirus, Ebolavirus, Bornavirus, Influenzavirus A, Influenzavirus B, Influenzavirus C, Thogotovirus, Isavirus, Orthobunyavirus, Hantavirus, Nairovirus, Phlebovirus, Tospovirus, Arenavirus, Ophiovirus, Tenuivirus, or Deltavirus. In specific embodiments, the negative-strand RNA virus is selected from the group consisting of Sendai virus, Measles virus, Mumps virus, Hendra virus, Newcastle disease virus, Human respiratory syncytial virus, Avian pneumovirus, Vesicular stomatitis Indiana virus, Rabies virus, Bovine ephemeral fever virus, Lettuce necrotic yellows virus, Potato yellow dwarf virus, Infectious hematopoietic necrosis virus, Lake Victoria marburgvirus, Zaire ebolavirus, Borna disease virus, Influenza virus, Thogoto virus, Infectious salmon anemia virus, Bunyamwera virus, Hantaan virus, Dugbe virus, Rift Valley fever virus, Tomato spotted wilt virus, Lymphocytic choriomeningitis virus, Citrus psorosis virus, Rice stripe virus, and Hepatitis delta virus. In preferred embodiments, the virus is an influenza virus (see below).

Where the virus is a positive-strand RNA virus, the virus may be from a family selected from the group consisting of Arteriviridae, Coronaviridae, Picornaviridae and Roniviridae. Furthermore, the virus may be a virus from a genus selected from the group consisting of Artetivirus, Coronavirus, Enterovirus, Torovirus, Okavirus, Rhinovirus, Hepatovirus, Cardiovirus, Aphthovirus, Parechovirus, Erbovirus, Kobuvirus and Teschovirus. In specific embodiments, the virus is selected from the group consisting of severe acute respiratory syndrome (SARS) virus, polio virus, Human enterovirus A (HEV-A), Human enterovirus B (HEV-B), Human enterovirus C, Human enterovirus D, Hepatitis A and Human rhinovirus A and B.

Where the virus is a double-stranded RNA virus, the virus may be from a family selected from the group consisting of Birnaviridae, Cystoviridae, Hypoviridae, Partitiviridae, Reoviridae and Totiviridae. Furthermore, the virus may be a virus from a genus selected from the group consisting of Aquabirnavirus, Avibirnavirus, Entomobimavirus, Cystovirus, Partitivirus, Alphacryptovirus, Betacryptovirus, Aquareovirus, Coltivirus, Cypovirus, Fijivirus, Idnoreovirus, Mycoreovirus, Orbivirus, Orthoreovirus, Oryzavirus, Phytoreovirus, Rotavirus and Seadornavirus.

Preferred viruses for use with the invention are rotaviruses. Reverse genetics with these viruses is currently difficult due to the poor efficiency of the viral rescue and the methods of the invention can therefore facilitate the rescue of this virus.

The present invention is also particularly suitable for viruses which undergo rapid mutation and where the recombinant approach allows for a more rapid isolation of the virus which can then be further propagated to obtain suitable vaccines. Therefore, in another preferred embodiment the virus is influenza.

Influenza Viruses

Influenza viruses are particularly suitable for use in the methods of the present invention, particularly influenza A viruses and influenza B viruses, as reverse genetics for this virus has been well characterized. Influenza viruses are segmented negative strand RNA viruses Influenza A and B viruses have eight segments, whereas influenza C virus has seven. The virus requires at least four viral proteins (PB1, PB2, PA and nucleoprotein) to initiate replication and transcription.

Reverse genetics for influenza A and B viruses can be practised with 12 plasmids to express the four required proteins and all eight genome segments. To reduce the number of constructs, however, a plurality of RNA polymerase I transcription cassettes (for viral RNA synthesis) can be included on a single plasmid (e.g. sequences encoding 1, 2, 3, 4, 5, 6, 7 or all 8 influenza vRNA segments), and a plurality of protein-coding regions with RNA polymerase II promoters on another plasmid (e.g. sequences encoding 1, 2, 3, 4, 5, 6, 7 or 8 influenza mRNA transcripts) [21]. It is also possible to include one or more influenza vRNA segments under control of a pol I promoter and one or more influenza protein coding regions under control of another promoter, in particular a pol II promoter, on the same plasmid. As described above, this is preferably done by using bi-directional plasmids.

Preferred aspects of the reference 21 method involve: (a) PB1, PB2 and PA mRNA-encoding regions on a single plasmid; and (b) all 8 vRNA encoding segments on a single plasmid. Including the neuraminidase (NA) and hemagglutinin (HA) segments on one plasmid and the six other segments on another plasmid is particularly preferred as newly emerging influenza virus strains usually have mutations in the NA and/or HA segments. Therefore, in this embodiment, only the vector comprising the HA and NA sequence needs to be replaced.

Preferred expression systems for influenza A viruses encode genome segments derived from a plurality of different wild-type strains. The system may encode 1 or more (e.g. 1, 2, 3, 4, 5 or 6) genome segments from a PR/8/34 strain (A/Puerto Rico/8/34), but usually this/these will not include the PR/8/34 HA segment and usually will not include the PR/8/34 NA segment, Thus the system may encode at least one of segments NP, M, NS, PA, PB1 and/or PB2 (possibly all six) from PR/8/34.

Other useful expression systems for influenza A viruses may encode 1 or more (e.g. 1, 2, 3, 4, 5 or 6) genome segments from an AA/6/60 influenza virus (A/Ann Arbor/6/60), but usually this/these will not include the AA/6/60 HA segment and usually will not include the AA/6/60 NA segment. Thus the system may encode at least one of segments NP, M, NS, PA, PB1 and/or PB2 (possibly all six) from AA/6/60.

The system may encode 1 or more genome segments from an A/California/4/09 strain e.g. the HA segment and/or the NA segment. Thus, for instance, the HA gene segment may encode a H1 hemagglutinin which is more closely related to SEQ ID NO: 1 than to SEQ ID NO: 2 (i.e. has a higher degree sequence identity when compared to SEQ ID NO: 1 than to SEQ ID NO: 2 using the same algorithm and parameters). SEQ ID NOs: 1 and 2 are 80% identical. Similarly, the NA gene may encode a N1 neuraminidase which is more closely related to SEQ ID NO: 3 than to SEQ ID NO: 4. SEQ ID NOs: 3 and 4 are 82% identical.

Expression systems for influenza B viruses may encode genome segments derived from a plurality of different wild-type strains. The system may encode 1 or more (e.g. 1, 2, 3, 4, 5 or 6) genome segments from a AA/1/66 influenza virus (B/Ann Arbor/1/66), but usually this/these will not include the AA/1/66 HA segment and usually will not include the AA/1/66 NA segment. Thus the system may encode at least one of segments NP, M, NS, PA, PB1 and/or PB2 from AA/1/66.

Viral segments and sequences from the A/PR/8/34, AA/6/60, AA/1/66, A/Chile/1/83 and A/California/04/09 strains are widely available. Their sequences are available on the public databases e.g. GI:89779337, GI:89779334, GI:89779332, GI:89779320, GI:89779327, GI:89779325, GI:89779322, GI:89779329.

A reverse genetics system for influenza virus may include an expression construct which leads to expression of an accessory protein in the host cell. For instance, it can be advantageous to express a non-viral serine protease (e.g. trypsin).

Vaccine

In one aspect, the invention utilises virus produced according to the methods of the invention to produce vaccines.

Vaccines (particularly for influenza virus) are generally based either on live virus or on inactivated virus. Inactivated vaccines may be based on whole virions, 'split' virions, or on purified surface antigens. Antigens can also be presented in the form of virosomes. The invention can be used for manufacturing any of these types of vaccine.

Where an inactivated virus is used, the vaccine may comprise whole virion, split virion, or purified surface antigens (for influenza, including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 22-27, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkyithioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLUSHIELD™ products.

The method of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 & 18 of reference 28). Live viruses include MedImmune's FLUMIST™ product (trivalent live virus).

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome [29] (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

The virus may be attenuated. The virus may be temperature-sensitive. The virus may be cold-adapted. These three features are particularly useful when using live virus as an antigen.

HA is the main immunogen in current inactivated influenza vaccines, and vaccine doses are standardised by reference to HA levels, typically measured by SRID. Existing vaccines typically contain about 15 µg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [30,31]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 3.75, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

Influenza virus strains for use in vaccines change from season to season. In inter-pandemic periods, vaccines typically include two influenza A strains (H1N1 and H3N2) and one influenza B strain, and trivalent vaccines are typical. The invention may also use pandemic viral strains (i.e. strains to which the vaccine recipient and the general human population are immunologically naïve, in particular of influenza A virus), such as H2, H5, H7 or H9 subtype strains, and influenza vaccines for pandemic strains may be monovalent or may be based on a normal trivalent vaccine supplemented by a pandemic strain. Depending on the season and on the nature of the antigen included in the vaccine, however, the invention may protect against one or more of HA subtypes H1, H2, H3, H4, H5, H6, H7, H8, H9, H10, H11, H12, H13, H14, H15 or H16. The invention may protect against one or more of influenza A virus NA subtypes N1, N2, N3, N4, N5, N6, N7, N8 or N9.

As well as being suitable for immunizing against inter-pandemic strains, the compositions of the invention are particularly useful for immunizing against pandemic or potentially-pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) it is capable of being transmitted horizontally in the human population; and (c) it is pathogenic to humans. A virus with H5 hemagglutinin type is preferred for immunizing against pandemic influenza, such as a H5N1 strain. Other possible strains include H5N3, H9N2, H2N2, H7N1 and H7N7, and any other emerging potentially pandemic strains. The invention is particularly suitable for protecting against potential pandemic virus strains that can or have spread from a non-human animal population to humans, for example a swine-origin H1N1 influenza strain. The invention is then suitable for vaccinating humans as well as non-human animals.

Other strains whose antigens can usefully be included in the compositions are strains which are resistant to antiviral therapy (e.g. resistant to oseltamivir [32] and/or zanamivir), including resistant pandemic strains [33].

Compositions of the invention may include antigen(s) from one or more (e.g. 1, 2, 3, 4 or more) influenza virus strains, including influenza A virus and/or influenza B virus. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [34], including antigens from two influenza A virus strains and two influenza B virus strains, or three influenza A virus strains and one influenza B virus strain.

Pharmaceutical Compositions

Vaccine compositions manufactured according to the invention are pharmaceutically acceptable. They usually include components in addition to the antigens e.g. they typically include one or more pharmaceutical carrier(s) and/or excipient(s). As described below, adjuvants may also be included. A thorough discussion of such components is available in reference 35.

Vaccine compositions will generally be in aqueous form. However, some vaccines may be in dry form, e.g. in the form of injectable solids or dried or polymerized preparations on a patch.

Vaccine compositions may include preservatives such as thiomersal or 2-phenoxyethanol. It is preferred, however, that the vaccine should be substantially free from (i.e. less than 5 μg/ml) mercurial material e.g. thiomersal-free [26,36]. Vaccines containing no mercury are more preferred, α-tocopherol succinate can be included as an alternative to mercurial compounds [26]. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [37], but keeping osmolality in this range is nevertheless preferred.

Vaccine compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may included less than 1 mg/ml of each of octoxynol-10 and polysorbate 80. Other residual components in trace amounts could be antibiotics (e.g. neomycin, kanamycin, polymyxin B).

A vaccine composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Host Cell DNA

Where virus has been isolated and/or grown on a cell line, it is standard practice to minimize the amount of residual cell line DNA in the final vaccine, in order to minimize any oncogenic activity of the DNA.

Thus a vaccine composition prepared according to the invention preferably contains less than 10 ng (preferably less than 1 ng, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 38 & 39, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [40].

Adjuvants

Compositions of the invention may advantageously include an adjuvant, which can function to enhance the immune responses (humoral and/or cellular) elicited in a subject who receives the composition. Preferred adjuvants comprise oil-in-water emulsions. Various such adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used, 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Another preferred oil is α-tocopherol (see below).

Mixtures of Oils can be Used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Where the vaccine contains a split virus, it is preferred that it contains free surfactant in the aqueous phase. This is advantageous as the free surfactant can exert a 'splitting effect' on the antigen, thereby disrupting any unsplit virions and/or virion aggregates that might otherwise be present. This can improve the safety of split virus vaccines [41].

Preferred emulsions have an average droplets size of <1 μm e.g. ≤750 nm, ≤500 nm, ≤400 nm, ≤300 nm, ≤250 nm, ≤220 nm, or ≤200 nm, or smaller. These droplet sizes can conveniently be achieved by techniques such as microfluidisation.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85, This adjuvant is known as 'MF59' [42-44], as described in more detail in Chapter 10 of ref. 45 and chapter 12 of ref. 46. The MF59 emulsion advantageously includes citrate ions e.g. 10 mM sodium citrate buffer.
- An emulsion of squalene, DL-α-tocopherol, and polysorbate 80 (Tween 80). The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2 or at a weight ratio of about 11:5, One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [47].
- An emulsion of squalene, a tocopherol, and a Triton detergent (e.g. Triton X-100). The emulsion may also include a 3d-MPL (see below). The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [48] (0.05-1% Thr-MDP, 5% squalane, 2.5% Pluronic L121 and 0.2% polysorbate 80). It can also be used without the Thr-MDP, as in the "AF" adjuvant [49] (5% squalane, 1.25% Pluronic L121 and 0.2% polysorbate 80). Microfluidisation is preferred.
- An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [50]. The emulsion may also include one or more of alditol; a cryoprotective agent (e.g. a sugar, such as dodecylmaltoside and/or sucrose); and/or an alkylpolyglycoside. The emulsion may include a TLR4 agonist [51]. Such emulsions may be lyophilized
- An emulsion of squalene, poloxamer 105 and Abil-Care [52]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).
- An emulsion having from 0.5-50% of an oil, 0.1-10% of a phospholipid, and 0.05-5% of a non-ionic surfactant. As described in reference 53, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 54, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.
- An emulsion in which a saponin (e.g. QuilA or QS21) and a sterol (e.g. a cholesterol) are associated as helical micelles [55].
- An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [56].
- An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [56].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Packaging of Vaccine Compositions

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized, before the composition is added to it.

To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colourless glass.

A vial can have a cap (e.g. a Luer lock) adapted such that a pie-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. In the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

The invention provides a vaccine manufactured according to the invention. These vaccine compositions are suitable for administration to human or non-human animal subjects, such as pigs, and the invention provides a method of raising an immune response in a subject, comprising the step of administering a composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [57]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [58-60], oral [61], intradermal [62,63], transcutaneous, transdermal [64], etc.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, subjects who have taken an anti-viral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

MODES FOR CARRYING OUT THE INVENTION

Viral Rescue

Figure 1:
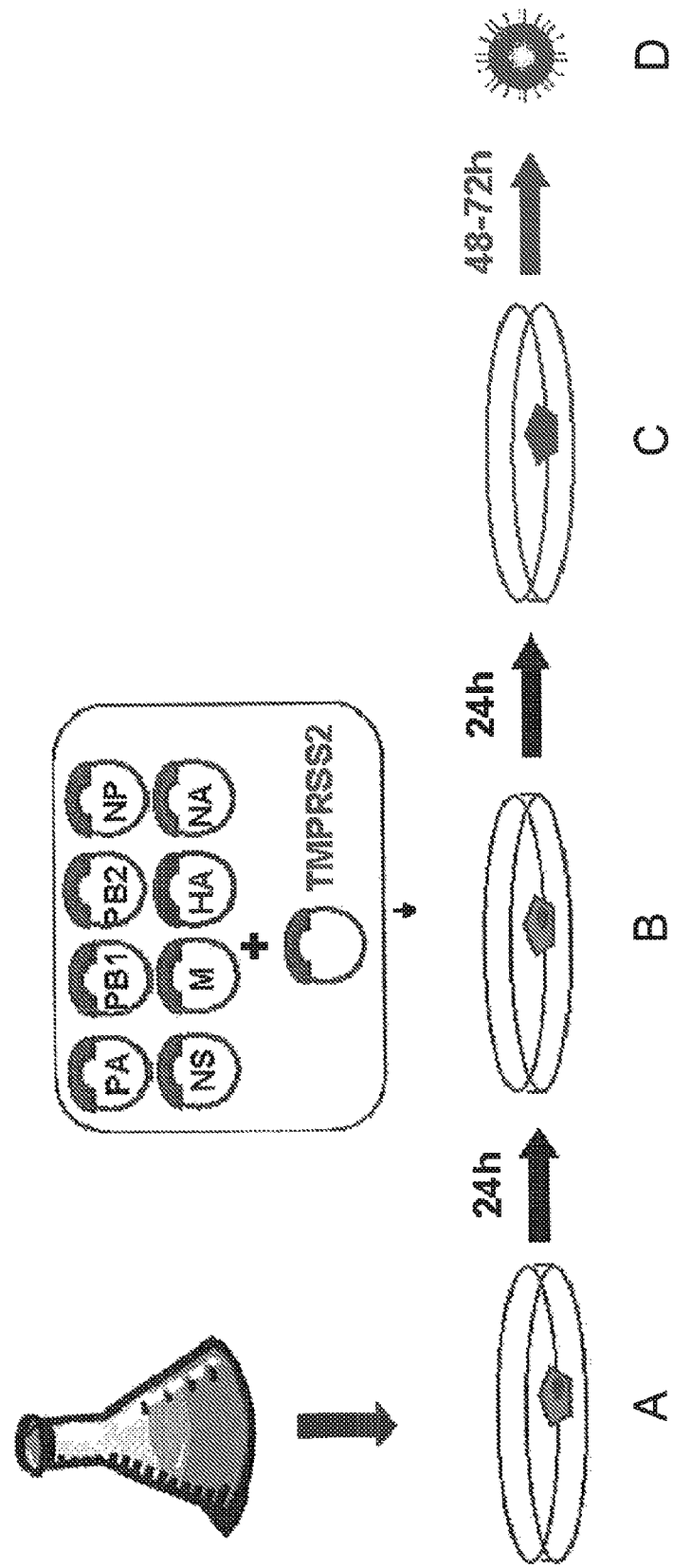
FIG. 1: Schematic representation of an embodiment of the present invention; MDCK 33016 suspension cells (cultured in CDM) are seeded in a 6-well dish A (in serum-free medium or DMEM+5% PBS); B: co-transfection MDCK 33016; C: wash 2×, change to serum-free DMEM, +trypzean, +/−fresh, uninfected MDCK cells, D: RG virus

MDCK 33016 cells were cultured in suspension in CDM media at a temperature of 37° C. A day before transfection $6 \times 10^5$ cells/well were seeded in a CELL-BIND™ 6 well dish in 2 mL DMEM medium with 5% FCS. In a parallel experiment the cells were seeded in the absence of FCS. The cells were incubated at 37° C. overnight.

The next day the seeded cells were transfected with Lipofectamine™ LTX Plus transfection reagent using the manufacturer's protocol. Briefly, 1 μg of each plasmid (PA, PB1, PB2, NP, NS, M, HA, NA plus TMPRSS2) was diluted in 500 μl of serum-free DMEM medium. 10 μl of Plus reagent was added directly to the diluted DNA. The mixture was incubated at room temperature Jim 5 minutes after which 25 μl of Lipofectamine was added to it. The mixture was then incubated at room temperature for 30 minutes. Following the incubation, the transfection reagent:DNA complex was added to the cells in a drop-wise manner. The cells were subsequently incubated at 37° C. for 24 hours.

Following the incubation, the medium was aspirated from the cells and a suspension of $4 \times 10^5$ MDCK 33016 cells in serum-free DMEM medium containing a 1:2000 dilution of Trypzean™ (1 mg/mL stock solution) was added to each well. In a parallel experiment, a 1:2000 dilution of Trypzean™ (1 mg/mL stock solution) alone, i.e. without addition of cells, was added to the transfected cells. The cells were then incubated at 37° C. for another 48 hours or until the cells were lysed after which the virus titre was determined using a Focus-Forming Assay.

Focus-Forming Assays

Uninfected MDCK cells were plated at a density of $6.25 \times 10^4$ cells/well in 48 well plates in 500 μl of DMEM with 10% FCS. The next day cells were infected with viruses in a volume of 100-150 μl for 2 hours at 37° C. The cells were infected with various dilutions of the virus. Two hours post-infection, the medium was aspirated and 500 μl of DMEM with 10% FCS was added to each well. The cells were incubated at 37° C. until the next day.

24 hours after infection, the medium was aspirated and the cells washed once with PBS. 500 μl of ice-cold 80% acetone in PBS was added to each well followed by incubation at 4° C. for 30 minutes. The acetone mix was aspirated and the cells washed once with PBST (PBS+0.1% Tween). 500 μl of 2% BSA in PBS was added to each well followed by incubation at room temperature (RT) for 30 minutes. 500 μl of a 1:6000 dilution of anti-NP was added in blocking buffer followed by incubation at RT for 2 hours. The antibody solution was aspirated and the cells washed twice with PBST. Secondary antibody (goat anti mouse) was added at a dilution 1:2000 in 500 μl blocking buffer and the plate was incubated at RT for 2 hours. The antibody solution was aspirated and the cells washed three times with PBST. 500 μl of KPL True Blue was added to each well and incubated for 10 minutes. The reaction was stopped by aspirating the True-Blue and washing once with $dH_2O$. The water was aspirated and the cells left to dry.

Results

Figure 2:
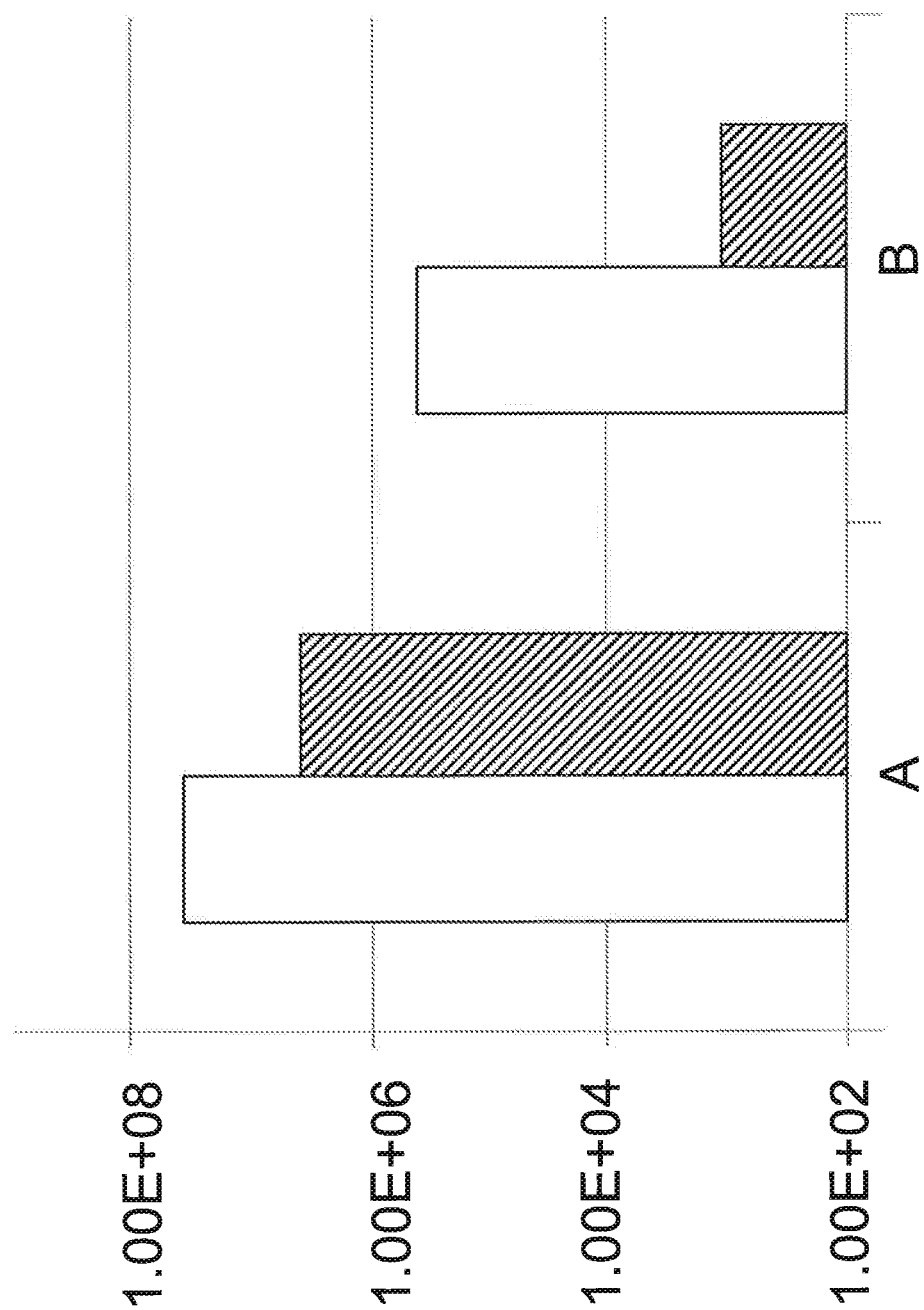
FIG. 2: Efficiency of influenza virus rescue in MDCK 33016 cells using the PR8-A/CA backbone; the y-axis shows infectious titre (FFU/mL); the open boxes show results with PR8-A/CA and 5% serum and the hatched boxes show results with PR8-A/CA and no serum; A indicates that fresh uninfected cells were added; B indicates that no fresh uninfected cells were added.
Figure 3:
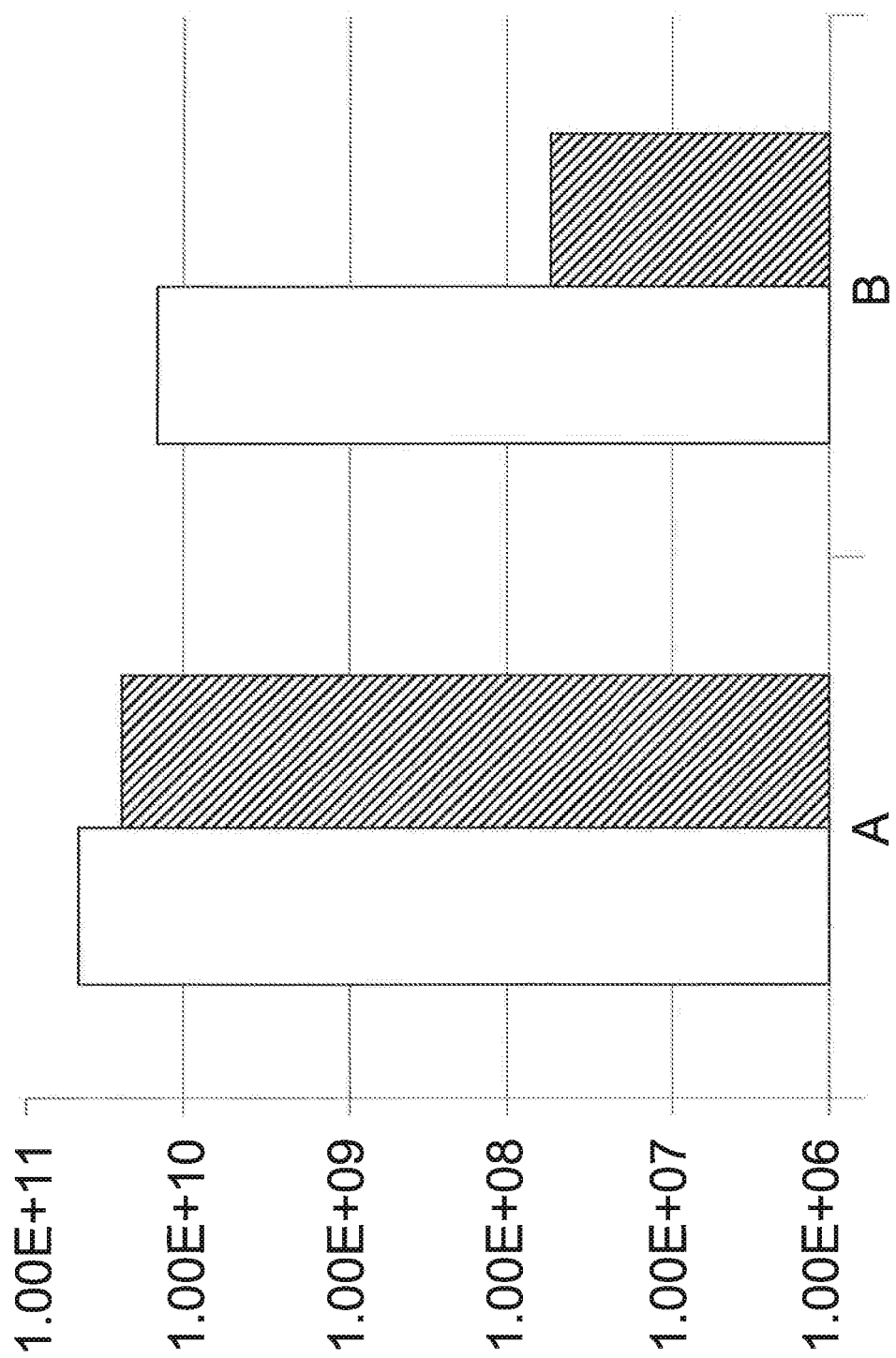
FIG. 3: Efficiency of influenza virus rescue in MDCK 33016 cells using the A/WSN/33 backbone; the y-axis shows infectious titre (FFU/mL); the open boxes show results with WSN and 5% serum and the hatched boxes show results with WSN and no serum; A indicates that fresh uninfected cells were added; B indicates that no fresh uninfected cells were added.
Figure 4:
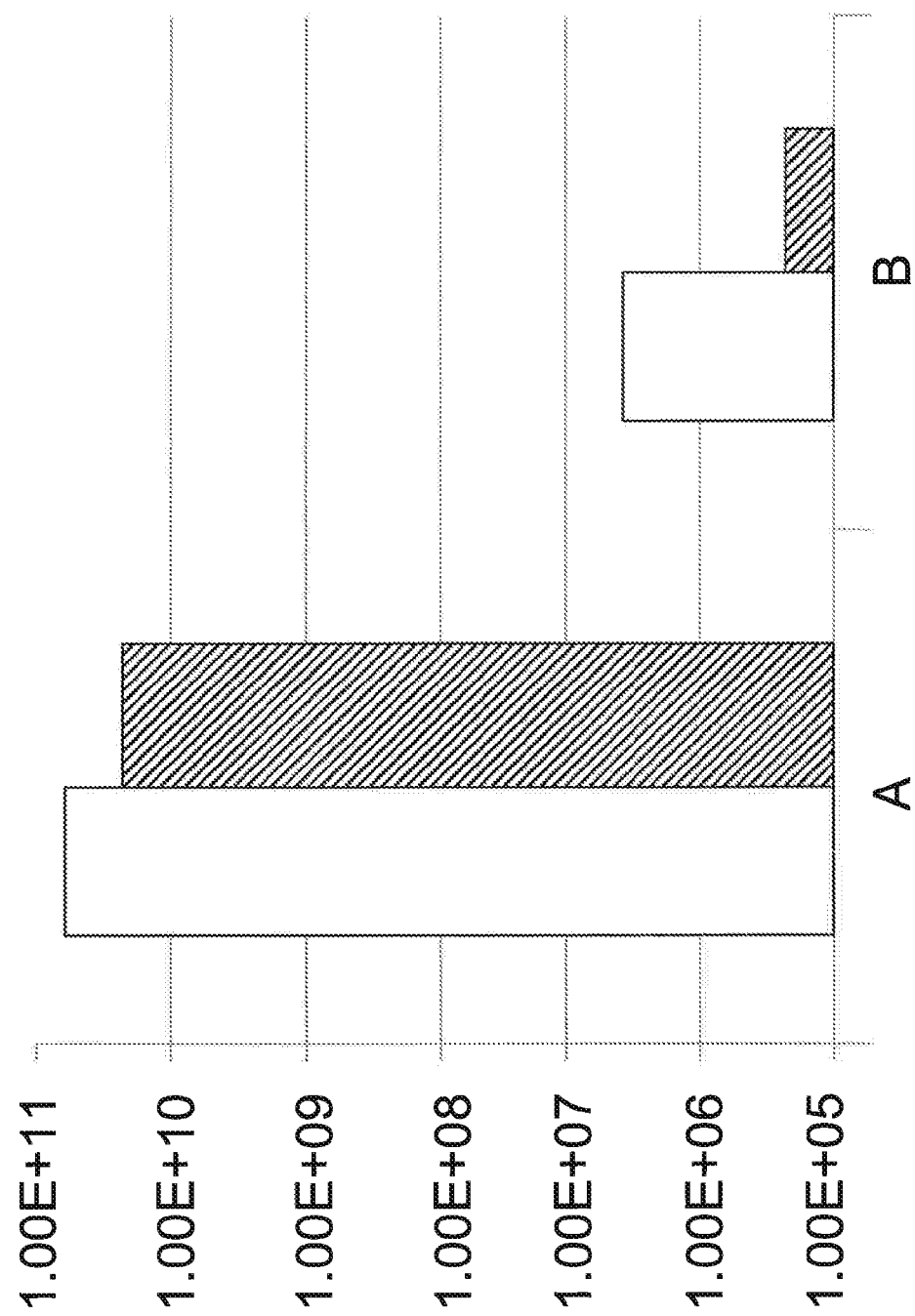
FIG. 4: Efficiency of influenza virus rescue in MDCK 33016 cells using the PR8-WSN backbone, the y-axis shows FFU/mL; the open boxes show results with PR8-WSN and 5% serum and the hatched boxes show results with PR8-WSN and no serum; A indicates that fresh uninfected cells were added; B indicates that no fresh uninfected cells were added.

The results of the focus forming assay with three different viral backbones is shown in FIGS. 2-4. The results show the efficiency of the viral rescue with and without the addition of cells 24 hours after infection. As can be seen, in all cases the efficiency of the viral rescue increased by up to three-fold in the experiments where cells were added 24 hours after transfection compared to the experiments where no cells were added. This increase in efficiency can be seen with all tested viral backbones and under both serum-containing and serum-free conditions.

It will be understood that the invention has been described by way of example only and modifications may be made whilst remaining within the scope and spirit of the invention.

DEPOSIT INFORMATION

A deposit of the microorganism MDCK 33016 (DSM ACC2219) was deposited on Jun. 7, 1995 according to the Budapest Treaty in the International Depository Authority DSM-Deutsche Sammlung Von Mikroorganismen and Zelkulturen GmbH, Mascheroder Weg 1b, D-38124 Braunschweig.

REFERENCES

[1] Racaniello and Baltimore (1981) Science 214:916-919
[2] Kaplan et al. (1985) Proc Natl Acad Sci USA 82: 8424-8428
[3] Fodor et al. (1999) J. Virol 73(11):9679-9682
[4] Hoffmann et al. (2002) Proc Natl Acad Sci USA 99: 11411-11416
[5] Kobayashi et al. (2007) Cell Host Microbe 19; 1(2):147-57
[6] WO2009/000891
[7] Sambrook et al, Molecular Cloning: A Laboratory Manual, 2 ed., 1989, Cold Spring Harbor Press, Cold Spring Harbor, N.Y
[8] Kistner et al, (1998) Vaccine 16:960-8,
[9] Kistner et al. (1999) Dev Biol Stand 98:101-110,
[10] Bruhl et al. (2000) Vaccine 19:1149-58.
[11] Pau et al. (2001) Vaccine 19:2716-21,
[12] www.atcc.org/
[13] locus.umdnj.edui
[14] WO97/37000.
[15] Brands et al. (1999) Dev Biol Stand 98:93-100.
[16] Halperin et al. (2002) Vaccine 20:1240-7.
[17] EP-A-1260581 (WO01/64846)
[18] WO2006/071563
[19] WO2005/113758
[20] WO97/37001
[21] Neumann et al. (2005) Proc Natl Acad Sci USA 102: 16825-9
[22] WO02/28422.
[23] WO02/067983.
[24] WO02/074336.
[25] WO01/21151.
[26] WO02/097072.
[27] WO2005/113756.
[28] Vaccines. (eds. Plotkins & Orenstein). 4th edition, 2004, ISBN: 0-7216-9688-0
[29] Huckriede et al. (2003) Methods Enzymol 373:74-91.
[30] Treanor et al. (1996) J Infect Dis 173:1467-70.
[31] Keitel et al. (1996) Clin Diagn Lab Immunol 3:507-10.
[32] Herlocher et al. (2004) J Infect Dis 190(9):1627-30.
[33] Le et al. (2005) Nature 437(7062):1108.
[34] WO2008/068631.
[35] Gennaro (2000) Remington: The Science and Practice of Pharmacy. 20th edition, ISBN: 0683306472.
[36] Banzhaf (2000) Immunology Letters 71:91-96.
[37] Nony et al. (2001) Vaccine 27:3645-51.
[38] EP-B-0870508.
[39] U.S. Pat. No. 5,948,410.
[40] WO2007/052163.
[41] WO2007/052061
[42] WO90/14837.
[43] Podda & Del Giudice (2003) Expert Rev Vaccines 2:197-203.
[44] Podda (2001) Vaccine 19: 2673-2680.
[45] Vaccine Design: The Subunit and Adjuvant Approach (eds. Powell R. Newman) Plenum Press 1995 (ISBN 0-306-44867-X).
[46] Vaccine Adjuvants: Preparation Methods and Research Protocols (Volume 42 of Methods in Molecular Medicine series). ISBN: 1-59259-083-7. Ed. O'Hagan.
[47] WO2008/043774.
[48] Allison & Byars (1992) Res Immunol 143:519-25.
[49] Hariharan et al. (1995) Cancer Res 55:3486-9.
[50] US-2007/014805.
[51] US-2007/0191314.
[52] Suli et al. (2004) Vaccine 22(25-26):3464-9.
[53] WO95/11700.
[54] U.S. Pat. No. 6,080,725.
[55] WO2005/097181.
[56] WO2006/113373.
[57] Potter & Oxford (1979) Br Med Bull 35: 69-75.
[58] Greenbaum et al, (2004) Vaccine 22:2566-77.
[59] Zurbriggen et al. (2003) Expert Rev Vaccines 2:295-304.
[60] Piascik (2003) J Am Pharm Assoc (Washington D.C.). 43:728-30.
[61] Mann et al. (2004) Vaccine 22:2425-9.
[62] Halperin et al. (1979) Am J Public Health 69:1247-50.
[63] Herbert et al. (1979) J Infect Dis 140:234-8.
[64] Chen et al. (2003) Vaccine 21:2830-6.

---

The invention claimed is:

1. A method for preparing an influenza virus comprising the steps of (i) transfecting a culture of mammalian kidney cells with at least one expression construct encoding an influenza RNA molecule; (ii) adding untransfected mammalian kidney cells to the transfected cells of step (i) to provide a mixture of cells, wherein the untransfected cells are of the same type as the cells of step (i); and (iii) culturing the mixture of cells from step (ii) in order to produce influenza virus.

2. A method for preparing an influenza virus comprising the steps of (i) transfecting a culture of MDCK cells with at least one expression construct encoding an influenza RNA molecule; (ii) adding untransfected MDCK cells to the transfected MDCK cells of step (i) to provide a mixture of MDCK cells; and (iii) culturing the mixture of MDCK cells in order to produce influenza virus.

3. A method for preparing an influenza virus for vaccine manufacture, comprising steps (i)-(iii) of claim 2, and further comprising (iv) purifying the virus obtained in step (iii).

4. The method of claim 1, wherein the mammalian kidney cell is a VERO or MDCK cell.

5. The method of claim 2, wherein the MDCK cell is the cell line MDCK 33016 (DSM ACC2219).

6. The method of claim 3, further comprising the step of formulating the virus purified in step (iv) into a vaccine.

7. The method of claim 1, wherein the cells are cultured in suspension.

8. The method of claim 1, wherein the cells are cultured adherently.

* * * * *